United States Patent
Oudard

[11] Patent Number: 5,571,556
[45] Date of Patent: Nov. 5, 1996

[54] PULVERULENT ORGANOMETALLIC COMPOUNDS INTENDED FOR FORMING A TIN OXIDE FILM ON A SUBSTRATE, METHOD OF USING SAME AND THUS COATED SUBSTRATE

[75] Inventor: Jean-Francois Oudard, Thiescourt, France

[73] Assignee: Saint-Gobain Vitrage International, Courbevoie, France

[21] Appl. No.: 261,705

[22] Filed: Jun. 17, 1994

[30] Foreign Application Priority Data

Jun. 17, 1993 [FR] France .................................. 93 07335

[51] Int. Cl.$^6$ ...................................................... B05D 5/12
[52] U.S. Cl. .......................... 427/108; 427/162; 427/165; 427/186; 427/226; 427/126.2; 427/126.3
[58] Field of Search ............................. 427/126.2, 126.3, 427/226, 185, 108, 165, 162

[56] References Cited

U.S. PATENT DOCUMENTS 4,401,695  8/1983  Sopko ...................... 427/180
5,387,433  2/1995  Balian et al. ............... 427/263

FOREIGN PATENT DOCUMENTS

| 0103511 | 3/1984  | European Pat. Off. . |
| 0106744 | 4/1984  | European Pat. Off. . |
| 0178956 | 4/1986  | European Pat. Off. . |
| 0192009 | 8/1986  | European Pat. Off. . |
| 0196178 | 10/1986 | European Pat. Off. . |
| 0364337 | 4/1990  | European Pat. Off. . |

*Primary Examiner*—Janyce Bell
*Attorney, Agent, or Firm*—Oblon, Spivak, McClelland, Maier & Neustadt, P.C.

[57] ABSTRACT

A pulverulent organometallic compound containing tin and a halogen, notably fluorine, is pyrolyzed by heating on the surface of a transparent substrate, notably of glass, in order to form a film of tin oxide doped with a halogen. The coated substrate has improved infrared radiation and/or electrical properties. The granulometry of the organometallic compound is chosen such that the diameter of the particles $d_{90}$ is between 40 and 200 microns.

9 Claims, No Drawings

PULVERULENT ORGANOMETALLIC COMPOUNDS INTENDED FOR FORMING A TIN OXIDE FILM ON A SUBSTRATE, METHOD OF USING SAME AND THUS COATED SUBSTRATE

BACKGROUND OF THE INVENTION

1. Field of the Invention

The invention relates to pulverulent organometallic compounds intended for forming a film of tin oxide on a transparent substrate such as of glass, by a pyrolysis technique. The invention also concerns a method of depositing by pyrolysis and the substrate thus coated.

2. Discussion of the Background.

It is known to coat substrates of glass with thin films of a doped metallic oxide, and notably films of tin oxide doped with a halogen-containing, generally fluorine-containing, compound in order to give them certain properties, including properties affecting infrared radiation and/or electrical conduction properties. In this way it is possible to obtain low-emissivity or heating glass panes.

Various techniques exist for depositing films onto a substrate, including the technique known as powder pyrolysis. This technique involves projecting suitable organometallic compounds, i.e., halogenated stannic compounds, in the form of particles in suspension in a carrier as, directly onto the surface of a glass substrate raised to a high temperature, for example on the order of 400° to 650° C. On contact with the hot glass, the particles decompose leaving an oxide film. This is a proven technique, which has the advantage of allowing a continuous deposition onto a ribbon glass in a production line of a "float" installation and which enables quality coatings to be obtained. Suitable devices for carrying out this technique are described for example, in EP-B-0 125 153 (U.S. Pat. No. 4,533,571) and EP-A-0 374 023 (U.S. Pat. No. 5,005,769).

Various types of pulverulent organometallic compounds are suitable for obtaining films of tin oxide doped with fluorine ($SnO_2$:F). Thus, there are known compounds simultaneously containing tin and fluorine, such as dipropyl tin ditrifluoroacetate $(C_3H_7)_2 Sn(CF_3COO)_2$ and dibutyl tin ditrifluoroacetate $(C_4H_9)_2 Sn(CF_3COO)_2$ described in EP-B-0 106 744 and dibutyl tin difluoride $(C_4H_9)_2SnF_2$, termed DBTF, a synthesis of which is described in EP-B-0 178 956.

It is also known from EP-B-0 039 256 to use a stannic compound without halogen, such an dibutyl tin oxide (n-$C_4H_9)_2$SnO, termed DBTO, which is associated with another compound carrying halogen, such as DBTF. For all these compounds, particles having fairly small particle sizes are chosen, with at most mean particle diameters on the order of 15 to 20 microns and preferably particle diameters all below 20 microns, in order to facilitate bringing them into suspension in the carrier gas and their homogeneous flow from the distribution devices to the surface of the substrate to be coated.

As noted above, the coatings obtained from these pulverulent compounds have an optical appearance and satisfactory performance. Thus, in conformity with the teaching of EP-B-0 125 153 and EP-A-0 374 023, already referred to above, it is possible to obtain films of $SnO_2$:F having a uniform thickness and an emissivity which can be up to 0.25 from DBTF powders having a granulometry of less than 20 microns.

Attempts have been made to reduce still further the emissivity of such pyrolyzed films by altering the deposition conditions, such as the temperature of the substrate, or by increasing the thickness of the films. There are limits, however, to these optimizations if only because they create additional costs in terms of energy consumed and/or raw materials. Moreover, increasing the thickness of the film may modify its optical appearance in an undesired manner and the gain in emissivity progressively dwindles with this increase in thickness.

A need continues to exist for methods of improving, by various means, the properties of conductivity and/or electrical conductivity of the pyrolyzed films of doped tin oxide, and to achieve this result without causing difficulties and/or additional costs in production.

SUMMARY OF THE INVENTION

Accordingly, one object of this invention is a pulverulent organometallic compound containing tin and a halogen, preferably fluorine, which can be pyrolyzed under the effect of heat on the surface of a transparent substrate, preferably of glass, in order to form thereon an oxide film doped with a halogen and possessing improved properties of infrared radiation and/or electrical properties.

This and other objects of the invention have been achieved by the pulverulent organometallic compound of the present invention.

DETAILED DESCRIPTION OF THE PREFERRED EMBODIMENTS

The compound according to this invention possesses a granulometry such that the diameter of the particles $d_{90}$ lies between 40 and 200 microns, preferably between 50 and 150 microns and more preferably between 60 and 100 microns.

It is preferable for the granulometry to be chosen in such a way that, in addition, the diameter of the particles $d_{10}$ shall lie between 8 and 30 microns, preferably between 10 and 20 microns. Likewise, its granulometry may also be chosen so that, in addition the diameter of the particles $d_{50}$ shall be between 20 and 60 microns, preferably between 25 and 50 micrometers.

The terms "$d_{90}$", "$d_{50}$", and "$d_{10}$", respectively, mean that 90%, 50% and 10% of the particles of the powder have a diameter lower than the value indicated. The value of d90 gives a clear idea of the size of the particles. When combined with the values $d_{10}$ and/or $d_{50}$, it states the distribution of the particle sizes within a given range of values of diameter.

The pulverulent organometallic compound of the present invention is obtained by selecting particles having the desired granulometry after preparing these compounds using known means such as described in EP-B-0 106 744 and EP-B-0 178 956. The desired granulometry is obtained using conventional means such as sieves, filters, etc.

The invention also includes a method of deposition which uses a pyrolysis technique and organometallic compounds containing tin and a halogen for the purpose of obtaining films of tin oxide doped with a halogen, preferably fluorine, on transparent substrates, and the granulometry of which is as defined above. Any pulverulent organometallic compound known to be used in the deposition of halogen doped tin oxide films may be used in the present invention.

Preferably, the organometallic compound chosen is "self-doping" in so far as it contain both tin and halogen, which avoids the need to make mixtures of compounds. Suitable compounds include dipropyl tin ditrifluoroacetate and dibutyl tin ditrifluoroacetate. A preferred example is DBTF.

As used herein, the term "halogen" means fluorine, chlorine, bromine and iodine.

As a part of this invention, it has been discovered that, surprisingly, choosing much higher particle granulometry than those generally specified enables films to be obtained which have significantly improved emissivity and electrical conductivity for given thicknesses of oxide films. Thus, the emissivity is less than 0.2 and can reach values of 0.16 to 0.18, while the electrical resistivity remains less than $8.0 \times 10^{-4}$ ohm.cm and preferably lies between $7.0 \times 10^{-4}$ and $5.5 \times 10^{-4}$ ohm.cm, for oxide film thicknesses preferably between 300 and 420 nm.

What is particularly advantageous is that this improvement in the performances of the doped tin oxide films is not achieved at the expense of ease of deposition of these films, nor at the expense of their optical quality. In fact, by deliberately choosing very high granulometries, it might on the contrary have been expected that problems of inhomogeneity of the powder-carrier gas suspension and problems in the flow of this suspension through the distribution devices might have arisen, but this was not the case in the range of granulometries chosen according to this invention.

The pulverulent organometallic compounds of the present invention are coated onto the surface of a transparent substrate, preferably a sheet of glass, in the form of a particle suspension in a carrier gas using conventional equipment. The surface of the transparent substrate is heated so that the pulverulent organometallic compound particle decompose on the hot surface leaving a doped oxide film. Preferably, the substrate is heated to a temperature of about 400–650° C.

The films obtained are uniform in thickness and have a homogeneous and satisfying visual appearance.

In order still further to improve this visual appearance, and preferably to guarantee a neutrality of coloration in reflection from the substrate at the side on which the doped tin oxide film is deposited, it is of course possible to interpose an intermediate coating between the substrate and the doped tin oxide film. This coating may be based upon a dielectric material composed, for example, of at least one metallic oxide chosen from the oxides of aluminum, titanium, zinc, tin or indium, as is known from FR-B-2 670 199 (U.S. Pat. No. 5,244,692), or based upon a silicon oxynitride and/or oxycarbide material, as is known from FR-A-2 677 639 (U.S. Pat. No. 5,304,394).

It is also possible to add an "external" coating in context with and covering the film of doped tin oxide, which is preferably based upon silicon oxide. The characteristics of the intermediate coatings, on the one hand, and external coatings, on the other hand, in terms of thickness and refractive index are advantageously chosen in conformity with those described in EP-A-0 544 577 or EP-A-0 573 325.

The present inventors have succeeded in correlating the increase in the performance of the tin oxide film with the increase in the size of the crystals of which it is composed. They have established empirically that the granulometry of the particles of the organometallic compounds has a direct influence upon the way in which the crystallization of the oxide film takes place, and notably upon the size of the crystals and upon their preferential orientation. Even though the sizes of the powder particles and of the crystals are very far from being of the same order, it does however appear that the larger the diameter of the particles of organometallic compounds, the more the crystals of the film will be of large size and the more they will have a pronounced orientation. This has the consequence that the number of "intercrystal" grain boundaries in the film decreases, increasing the mobility of the free electrons in the film and, therefore, increasing film electrical conductivity and lowering film emissivity, because the emissivity and conductivity are linked together.

By measuring experimentally the size of the crystals in the films, values on the order of 20 nanometers are effectively obtained, much higher than the values obtained for films produced by pyrolysis of powders of usual granulometry, for example with $d_{90}$ of 25 microns.

Using an organometallic compound powder of larger granulometry has another advantageous consequence, i.e., a non-negligible increase in the pyrolysis yield or pyrolysis efficiency. This efficiency is calculated by measuring the quantity in weight of organometallic compounds necessary to obtain an oxide film of a given thickness. Thus, it has been observed that this efficiency, quite unexpectedly increases by about 20% if a powder granulometry $d_{90}$ of 60 microns is chosen according to this invention, rather than a standard granulometry $d_{90}$ of 20 to 25 microns. This increase in efficiency leads to significant reductions in cost of raw materials, all the more so because the invention enables the film thicknesses to be modulated according to the performance levels desired and the organometallic quantities to be used. Thus, for equal film thicknesses, the emissivity and electrical resistivity fall if large granulometries according to this invention are used. It is, however, also possible to maintain similar emissivity and resistivity values by decreasing the thickness of the films.

The invention is now described in greater detail with reference to the following non-limiting examples.

EXAMPLES

These examples all relate to the deposition of a film of $SnO_2$:F of approximately 340 nm onto a 4mm thick substrate of silico-sodo-calcic float glass by pyrolysis of a powder comprising 100% DBTF using deposition conditions and equipment known from U.S. Pat. No. 4,533,571 and U.S. Pat. No. 5,005,769 incorporated herein by reference for more detailed information. The substrate was at a temperature of approximately 550° C. during the deposition. Example 1 is a reference example using standard low granulometries for the DBTF powder.

Table 1 below indicates, for each of Examples 1 to 7, the granulometries, expressed in microns, $d_{90}$, $d_{50}$ and $d_{10}$, for the chosen DBTF powders. The whole assembly of these granulometries enables the distribution of the particle diameters of each of the powders used to be thoroughly evaluated.

TABLE 1

|  | $d_{10}$ | $d_{50}$ | $d_{90}$ |
| --- | --- | --- | --- |
| Example 1 | 5 | 12–15 | 25 |
| Example 2 | — | — | 40 |
| Example 3 | — | — | 50 |
| Example 4 | 10–15 | 25–35 | 60 |
| Example 5 | 20 | 50 | 100 |
| Example 6 | — | — | 150 |
| Example 7 | — | — | 200 |

Table 2 below summarizes the characteristics of the films obtained from these seven DBTF powders; the emissivity (Epsilon) is shown without units, and the electrical resistivity (R) is in ohm.cm.

TABLE 2

|  | Epsilon | R |
|---|---|---|
| Example 1 | 0.25 | $10 \times 10^{-4}$ |
| Example 2 | 0.22 | $8.8 \times 10^{-4}$ |
| Example 3 | 0.20 | $8.0 \times 10^{-4}$ |
| Example 4 | 0.18 | $7.0 \times 10^{-4}$ |
| Example 5 | 0.16 | $5.5 \times 10^{-4}$ |
| Example 6 | 0.17 | $6 \times 10^{-4}$ |
| Example 7 | 0.18 | $7 \times 10^{-4}$ |

For two of the examples, Reference Example 1 on the one hand and Example 4 on the other hand, the sizes of the crystals in the SnO2:F films were evaluated by their X-ray spectra.

These evaluations were made by measuring the width at the mid-height of the peak shown in the X-ray spectra obtained, which corresponds to the ray (2,0,0) which has a much higher intensity than the other rays.

From the X-ray spectra obtained by analysis of the films according to Reference Example 1 on the one hand, and according to Example 4 of this invention on the other hand, it is established that the mean diameter of the crystals of a film obtained with powders of a standard granulometry (Example 1) is approximately 13 nanometers, whereas that of a film obtained with powders of a higher granulometry (Example 4) is in the region of 20 nanometers. The powder granulometries according to the invention, therefore, enable crystal sizes greater by more than 50% to be obtained.

Moreover, by comparing the two spectra, notably the number of peaks and their sizes, it is possible to obtain an indication with regard to the crystallization of the two films. It was found that the film according to Example 4 has crystals with a very marked orientation, much more so than in the case of the film according to Example 1.

The combination of larger size crystals and a more preferential crystalline orientation leads to the improved electrical properties established according to Table 2.

The conclusions that may be derived from these examples and results are as follows granulometries $d_{90}$ up to about 150 or even 200 microns cause no problems with the equipment. The deposition method, therefore, does not require any adaptation or modification of existing equipment. All of the substrates coated with these films have a high light transmission ($T_L$) of at least 70 to 75% according to illuminant $D_{65}$ and do not possess notable optical defects. In addition, it can be seen that the emissivity and resistivity decrease considerably when the granulometry increases.

The emissivity decreases by almost 30% if a granulometry $d_{90}$ of 60 microns is used rather than a granulometry $d_{90}$ of 25 microns and the same is true for the electrical resistivity.

These improvements are linked to a modification in the way in which the crystallization of the films takes place, the crystals having a tendency to be of considerably larger size, notably by at least 30% and even 50% and more, and having a more marked orientation.

Obviously, numerous modifications and variations of the present invention are possible in light of the above teachings. It is therefore to be understood that within the scope of the appended claims, the invention may be practiced otherwise than as specifically described herein.

What is claimed as new and is desired to be secured by letters patent of the United States is:

1. A method of forming a film on a transparent substrate, comprising the steps of:

depositing a pulverulent organometallic compound comprising tin and a halogen and having a particle diameter in which 90% of particles have a diameter less than between 40–200 microns and 10% of particles have a diameter greater than 40–200 microns, and in which 50% of particles have a diameter less than between 20–60 microns and 50% of particles have a diameter greater than 20–60 microns onto a transparent substrate; and pyrolyzing said deposited organometallic compound at a temperature of about 400–650° C. to form a film of tin oxide doped with said halogen on said substrate.

2. The method of claim 1, wherein said substrate is glass.

3. The method of claim 1, wherein said halogen is fluorine.

4. The method of claim 1, wherein 90% of particles have a diameter less than between 50–150 microns.

5. The method of claim 4, wherein 90% of particles have a diameter less than between 60–100 microns.

6. The method of claim 8, wherein 50% of particles have a diameter less than between 25–50 microns.

7. The method of claim 1, wherein said organometallic compound comprises dibutyl tin difluoride.

8. A method of forming a film on a transparent substrate, comprising the steps of:

depositing a pulverulent organometallic compound comprising tin and a halogen and having a particle diameter in which 90% of particles have a diameter less than between 40–200 microns and 10% of particles have a diameter greater than 40–200 microns, and in which 50% of particles have a diameter less than between 20–60microns and 50% of particles have a diameter greater than 20–60 microns onto a transparent substrate; and pyrolyzing said deposited organometallic compound at a temperature of about 400°–650° C. to form a film of tin oxide doped with said halogen on said substrate, wherein 10% of particles have a diameter less than between 8–30 microns and 90% of particles have a diameter greater than 8–30 microns.

9. The method of claim 8, wherein 10% of particle have a diameter less than between 10–20 microns.

* * * * *